(12) United States Patent
Lambert et al.

(10) Patent No.: US 10,039,855 B2
(45) Date of Patent: Aug. 7, 2018

(54) ELASTIC FIBER CONTAINING AN ANTI-TACK ADDITIVE

(75) Inventors: James Michael Lambert, Staunton, VA (US); Young D. Nguyen, Crozet, VA (US); Robert O. Waldbauer, Jr., Waynesboro, VA (US); Hong Liu, Waynesboro, VA (US)

(73) Assignee: INVISTA North America S.a.r.l., Wilmington, DE (US)

( * ) Notice: Subject to any disclaimer, the term of this patent is extended or adjusted under 35 U.S.C. 154(b) by 229 days.

(21) Appl. No.: 12/969,725

(22) Filed: Dec. 16, 2010

(65) Prior Publication Data

US 2011/0152810 A1 Jun. 23, 2011

Related U.S. Application Data

(60) Provisional application No. 61/289,800, filed on Dec. 23, 2009.

(51) Int. Cl.
| | |
|---|---|
| *D01F 1/10* | (2006.01) |
| *A61L 15/14* | (2006.01) |
| *A61L 15/24* | (2006.01) |
| *C08L 23/14* | (2006.01) |
| *D01F 6/30* | (2006.01) |
| *D01F 6/46* | (2006.01) |
| *C08K 5/09* | (2006.01) |
| *C08K 5/20* | (2006.01) |
| *C08L 9/00* | (2006.01) |

(52) U.S. Cl.
CPC ............... *A61L 15/14* (2013.01); *A61L 15/24* (2013.01); *C08L 23/14* (2013.01); *D01F 1/10* (2013.01); *D01F 6/30* (2013.01); *D01F 6/46* (2013.01); *C08K 5/09* (2013.01); *C08K 5/20* (2013.01); *C08L 9/00* (2013.01); *H01J 2237/3156* (2013.01); *Y10T 428/249921* (2015.04)

(58) Field of Classification Search
CPC ...... C08L 23/14; C08L 23/16; C08L 2666/02; C08K 5/09
USPC .................................. 442/97, 100, 328, 329
See application file for complete search history.

(56) References Cited

U.S. PATENT DOCUMENTS

| | | | | |
|---|---|---|---|---|
| 4,003,974 | A | * | 1/1977 | Chantry et al. ............ 264/210.8 |
| 4,540,753 | A | | 9/1985 | Cozewith et al. |
| 5,153,157 | A | | 10/1992 | Hlatky et al. |
| 5,241,025 | A | | 8/1993 | Hlatky et al. |
| 5,525,675 | A | * | 6/1996 | Masuda et al. ............... 525/240 |
| 6,232,374 | B1 | * | 5/2001 | Liu et al. ...................... 524/210 |
| 6,258,917 | B1 | * | 7/2001 | Slagel ........................ 264/176.1 |

(Continued)

FOREIGN PATENT DOCUMENTS

| | | |
|---|---|---|
| EP | 1017729 | 7/2000 |
| EP | 1233191 | 8/2002 |

(Continued)

OTHER PUBLICATIONS

Verstrate et al., Macromolecules, 1988, p. 3360, vol. 21.

(Continued)

*Primary Examiner* — Jeremy R Pierce
(74) *Attorney, Agent, or Firm* — Bridget C. Sciamanna; Kathleen A. Tyrrell

(57) ABSTRACT

Embodiments of the disclosure include elastomeric stretch fibers containing an anti-tack agent, methods of preparing the fiber, methods of using this fiber, articles including this fiber, and the like.

7 Claims, 1 Drawing Sheet

(56) References Cited

U.S. PATENT DOCUMENTS

| | | | |
|---|---|---|---|
| 6,342,565 | B1 | 1/2002 | Cheng et al. |
| 6,525,157 | B2 | 2/2003 | Cozewith et al. |
| 6,559,262 | B1 | 5/2003 | Weymouth et al. |
| 6,740,609 | B1* | 5/2004 | Peng et al. ............ 442/327 |
| 6,770,713 | B2 | 8/2004 | Hanke et al. |
| 6,881,800 | B2 | 4/2005 | Friedersdorf |
| 7,232,871 | B2 | 6/2007 | Datta et al. |
| 2002/0147273 | A1* | 10/2002 | Patel et al. ............ 525/93 |
| 2005/0215964 | A1 | 9/2005 | Autran et al. |
| 2006/0008643 | A1* | 1/2006 | Lin et al. ............. 428/364 |
| 2006/0011771 | A1* | 1/2006 | Manning, Jr. ....... B65H 49/16 242/564.4 |
| 2006/0293424 | A1* | 12/2006 | Tse et al. ............. 524/270 |
| 2007/0112127 | A1* | 5/2007 | Soediono et al. ..... 524/543 |
| 2008/0182940 | A1* | 7/2008 | Dharmarajan et al. ... 525/240 |
| 2009/0298964 | A1 | 12/2009 | Jacob et al. |

FOREIGN PATENT DOCUMENTS

| | | |
|---|---|---|
| EP | 1614699 | 1/2006 |
| WO | 91/009882 | 7/1991 |
| WO | 93/014132 | 7/1993 |
| WO | 94/003506 | 2/1994 |
| WO | 95/007941 | 3/1995 |
| WO | 99/052950 | 10/1999 |
| WO | 00/024792 | 5/2000 |
| WO | 00/024793 | 5/2000 |
| WO | 01/058912 | 8/2001 |
| WO | 02/036651 | 5/2002 |
| WO | 03/040095 | 5/2003 |
| WO | 03/040201 | 5/2003 |
| WO | 03/040202 | 5/2003 |
| WO | 03/040233 | 5/2003 |
| WO | 03/040442 | 5/2003 |
| WO | 05/049672 | 6/2005 |

OTHER PUBLICATIONS

Subramaniam, Rubber Technology, 1995, pp. 179-208.
Rudnick et al., Synthetic Lubricants and High-Performance Functional Fluids, 1999, pp. 357-392.

* cited by examiner

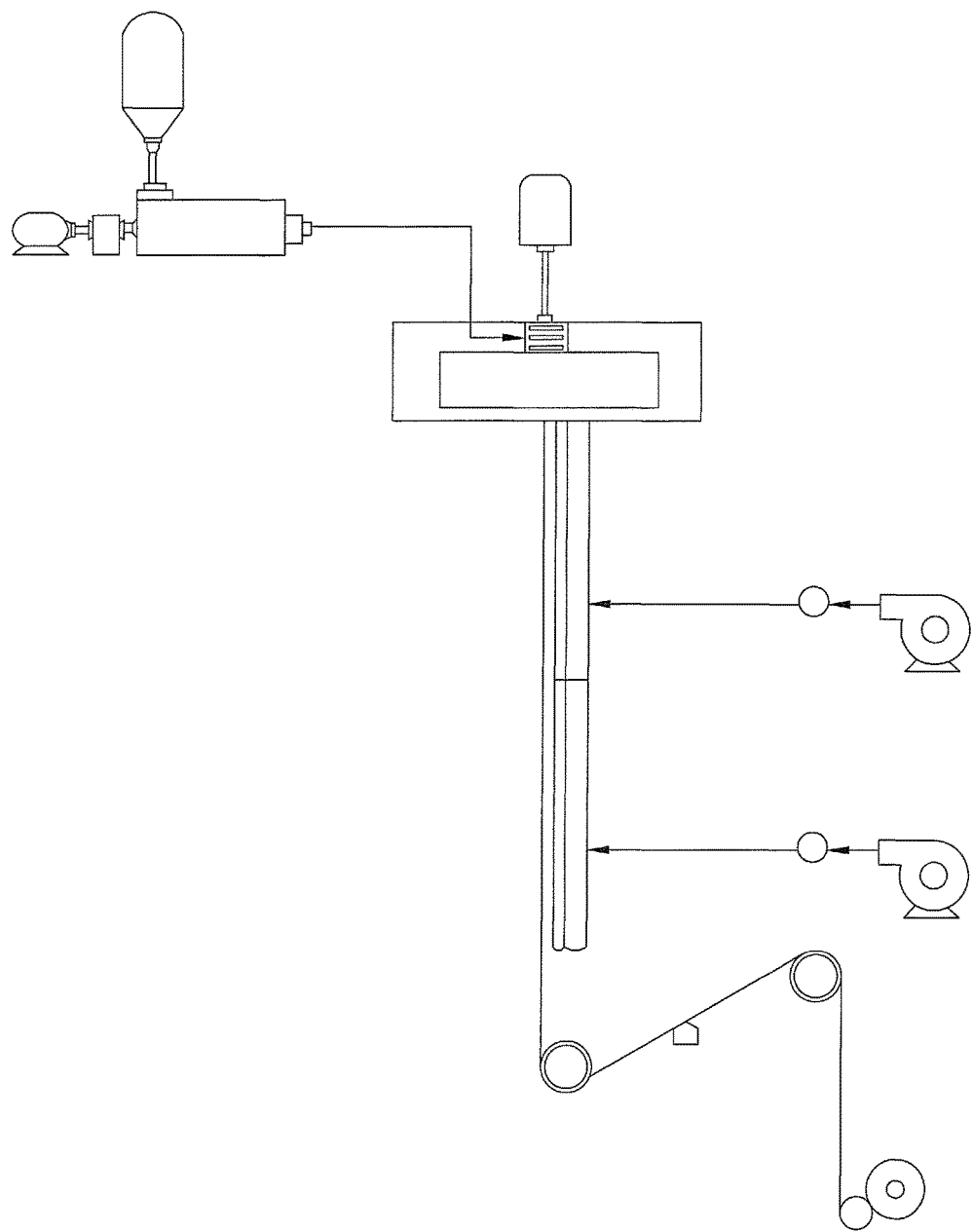

ELASTIC FIBER CONTAINING AN ANTI-TACK ADDITIVE

CROSS-REFERENCE TO RELATED APPLICATION

This application claims benefit of priority from Provisional Application No. 61/289,800, filed Dec. 23, 2009. This application hereby incorporates by reference Provisional Application No. 61/289,800 in its entirety.

FIELD OF THE DISCLOSURE

This disclosure relates to elastomeric propylene based polymer fibers having low tackiness without the use of silicone-based finishes and, more particularly, to such fibers having an anti-tack additive incorporated into the fiber.

BACKGROUND

Elastomeric fibers, such as those made from polyurethane (e.g., spandex), possess outstanding stretch and recovery properties making them suitable for many types of fibers, fabrics, laminates and other articles. Elastomeric polyolefin fibers (e.g., lastol, Dow Chemical's XLA™, ExxonMobil's Vistamaxx™) also have good stretch properties but, due to low melting points, are not always suitable for end-use where the end-use article (e.g., apparel) will be subject to high heats (e.g., during laundering). Elastomeric propylene based polymer fibers retain the stretch properties of non-cross-linked elastomeric propylene fibers, but can withstand much higher temperatures, making them more suitable for certain applications, such as fabrics for apparel.

However, all of the above elastomeric fibers, such as spandex and elastomeric polyolefin fibers, are known to display increased tackiness as compared to conventional, inelastic fibers. Because of their increased tackiness, these elastomeric fibers may cohere to each other or alternatively adhere to various surfaces. High tackiness becomes especially problematic in packaging where the fiber is wound around a core to form a bobbin, cake, or other such yarn package. The close proximity of the fibers plus the pressure on the fibers, especially near the core, may cause adjacent pieces of filament to cohere to each other, leaving the effected filament unusable since the fibers can be difficult to remove from the wound package without breaking. This problem becomes even more pronounced at the core, and is referred to as "core waste". After packaging, filament tackiness may increase during storage depending on time and temperature. Longer storage time and higher temperatures equate to increased tackiness and more core waste. Accordingly, a reduction in tackiness for elastomeric fibers would reduce core waste and increase cost effectiveness.

To reduce tackiness, a finish is applied to the yarn, such as spandex. These finishes can include silicon oil and metal stearates. The finishes are employed for lubricating the surfaces of elastomeric fibers and thus reducing the tackiness of the fibers. However, many such finishes, particularly silicone-based finishes interfere with downstream processing and render the treated fibers unsuitable for certain applications or require taking costly steps to remove the finish from the fibers. For instance, certain applications involve downstream processing that either necessitates no finish or where it is preferred to have no finish. In processes such as gluing heavy denier yarn into diapers and other disposable personal care articles, finish interferes with the adhesion of the glue to the fiber, resulting in less effective bonding of the elastomeric fiber and increased creep. Finish, particularly silicone-based finishes, can also interfere with fabric dyeing and finishing, thus necessitating costly and time-consuming steps to scour off the finish before dying and/or other downstream processing steps. However, such finishes are nearly uniformly employed in elastomeric fibers, since, as discussed above, fibers made with no finish are too tacky to unwind—breaking before they come off the spool. Even when anti-tack additives have been incorporated into spandex fibers to help reduce tackiness, surface finishes (such as finishing oils) are still required in order to prevent breakage and core-waste problems.

Thus, there is a need for improved elastomeric fibers, and fabrics and articles made therefrom, that possess reduced tack without the need for silicone-based finishes and processes for providing such fibers.

SUMMARY

Briefly described, embodiments of this disclosure include an elastomeric stretch fiber containing an anti-tack agent, methods of preparing the fiber, methods of using this fiber, articles including this fiber (such as, but not limited to, laminates, fabrics, garments, and textiles including the fiber), and the like.

One exemplary article of the present disclosure, among others, includes an elastomeric fiber, including: an elastomeric propylene based polymer and an anti-tack agent, where the fiber is substantially free of a silicone-based finish. In an embodiment, the anti-tack agent can be blended with the elastomeric propylene based polymer prior to spinning the fiber. In an embodiment, the anti-tack agent includes one or more of bis-stearamides, $TiO_2$, corn starch, talc, barium sulfate, lamellar clay, calcium carbonate, and mixtures thereof. In an embodiment the anti-tack agent can be an ethylene bis-stearamide. In an embodiment, the elastomeric fiber may include an optional diene and an optional cross-linking agent, and may optionally be crosslinked.

In addition, an embodiment of the present disclosure includes an article including an elastomeric fiber as described herein. In exemplary embodiments the article may include, but is not limited to, a fabric, a laminate, a stretch article, a disposable article, a garment, and the like.

One exemplary process for preparing an elastomeric propylene based polymer fiber, among others, includes: providing an elastomeric propylene based polymer; mixing an anti-tack agent with the elastomeric propylene based polymer; melt-spinning the polymer/anti-tack mixture into a fiber; and winding the fiber, where the fiber can be unwound without the application of a silicone-based finish to the surface of the fiber prior to winding. In embodiments, the mixing can occur during preparation of the elastomeric propylene based polymer pellets, chips, granules, and the like. In other embodiments, the mixing can occur during melt-spinning, such as by metering the anti-tack and propylene based polymer into the melt spinning machine. In other embodiments, the anti-tack can be used as a surface coating/dusting agent on the propylene based polymer pellets, chips or granules. In such embodiments, the anti-tack serves a dual purpose of keeping the pellets from sticking together (agglomerating) and from bridging in the feed throat of the spinning machine.

BRIEF DESCRIPTION OF THE DRAWINGS

Many aspects of this disclosure can be better understood with reference to the following drawings. The components in the drawings are not necessarily to scale.

FIG. 1 illustrates an exemplary system used to carry out the method of making the elastomeric fiber of the present disclosure.

DETAILED DESCRIPTION

Before the present disclosure is described in greater detail, it is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any methods and materials similar or equivalent to those described herein can also be used in the practice or testing of the present disclosure, the preferred methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present disclosure is not entitled to antedate such publication by virtue of prior disclosure. Further, the dates of publication provided could be different from the actual publication dates that may need to be independently confirmed.

As will be apparent to those of skill in the art upon reading this disclosure, each of the individual embodiments described and illustrated herein has discrete components and features that may be readily separated from or combined with the features of any of the other several embodiments without departing from the scope or spirit of the present disclosure. Any recited method can be carried out in the order of events recited or in any other order that is logically possible.

Embodiments of the present disclosure will employ, unless otherwise indicated, techniques of chemistry, fiber technology, textiles, and the like, which are within the skill of the art. Such techniques are fully explained in the literature.

The following examples are put forth so as to provide those of ordinary skill in the art with a complete disclosure and description of how to perform the methods and use the compositions and compounds disclosed and claimed herein. Efforts have been made to ensure accuracy with respect to numbers (e.g., amounts, temperature, etc.), but some errors and deviations should be accounted for. Unless indicated otherwise, parts are parts by weight, temperature is in ° C., and pressure is in atmospheres. Standard temperature and pressure are defined as 25° C. and 1 atmosphere.

Before the embodiments of the present disclosure are described in detail, it is to be understood that, unless otherwise indicated, the present disclosure is not limited to particular materials, reagents, reaction materials, manufacturing processes, or the like, as such can vary. It is also to be understood that the terminology used herein is for purposes of describing particular embodiments only, and is not intended to be limiting. It is also possible in the present disclosure that steps can be executed in different sequence where this is logically possible.

It must be noted that, as used in the specification and the appended claims, the singular forms "a," "an," and "the" include plural referents unless the context clearly dictates otherwise. Thus, for example, reference to "a support" includes a plurality of supports. In this specification and in the claims that follow, reference will be made to a number of terms that shall be defined to have the following meanings unless a contrary intention is apparent.

Definitions

As used herein, the term "anti-tack agent" or "anti-tack additive" refers to an additive or agent that includes compositions generally useful as fillers used in fiber/filament preparation that can reduce tackiness of elastomeric fibers and that is admixed with the fiber forming material at some point prior to fiber formation (e.g., during formation of the elastomeric polymer or during the melt-spinning process before fiber formation), and is thus incorporated into the formed fiber. This is in contrast to a "finish," "finishing agent," or "finishing oil" which, as used herein, is applied to the surface of a formed fiber.

As used herein, the term "fiber" refers to filamentous material that can be used in fabric and yarn as well as textile fabrication. One or more fibers can be used to produce a fabric or yarn. The yarn can be fully drawn or textured according to methods known in the art.

As used herein, the term "substantially free of", in reference to a chemical, indicates that the chemical is intended to be excluded from an object (e.g., a fiber); however, trace amounts of the chemical might be present in/on the object due to contamination, impurities, processing on shared equipment, and the like. In an embodiment, the term "substantially free of" refers to the object including less than about 0.001, less than about 0.01, less than about 0.05, less than about 0.1, less than about 0.5, less than about 1, or less than about 2 weight %, of the chemical in the object. In particular, the term "substantially free of", in reference to an additive (e.g., a finishing additive or agent), indicates that the additive is intended to be excluded from an object (e.g., a fiber); however, trace amounts of the additive might be present in/on the object due to contamination, impurities, processing on shared equipment, and the like.

As used herein, "elastomeric propylene based polymer" refers to an elastomeric polymer composition including a propylene backbone, as described in greater detail below. Exemplary propylene based polymers are described in US 2004/0236042 and WO05/049672 and in U.S. Pat. No. 6,881,800, each of which is hereby incorporated by reference. Exemplary commercially available elastomeric propylene based polymers useful in making the elastomeric fibers and articles of the present disclosure include Vistamaxx™ 1100 and Vistamaxx™ 2100 by ExxonMobil Corporation. In embodiments, the elastomeric propylene based polymer may also include additional components, such as, but not limited to, an optional diene and cross-linking agent (also referred to as a co-agent), to form a cross-linkable elastomeric propylene based polymer, such as described in US. Patent Application Publication No. 2009/0298964, which is hereby incorporated by reference herein, and as described in greater detail below. As used herein, the term "elastomeric propylene based polymer" refers to both types of formulations. Synthetic fibers made from the elastomeric propylene based polymers can be wound on a cylindrical core to form a supply package. Such fibers may be prepared by a melt-spinning or a dry-spinning process and can have any of a variety of cross-sections such as a round cross-section or a flat "tape-like" cross section.

Discussion

Embodiments of the present disclosure provide for an elastomeric fiber including an anti-tack agent incorporated into the fiber by combining the anti-tack agent with an elastomeric polypropylene-based polymer composition prior to spinning, methods of preparing the fiber, methods of using this fiber, laminates including the fiber, fabrics including the fiber, garments, textiles including the fiber, and the like. Embodiments of the present disclosure provide elastomeric fibers that provide good delivery of the fiber from the package or core. Embodiments of the present disclosure provide smooth and even delivery of the elastomeric fiber, which may reduce running bands, uneven drafting, pinching, breakage, and/or other damage of the fiber, as opposed to other elastomeric fibers that cause irregular delivery of the fibers. Embodiments of the present disclosure can be bound with other thermoplastic fibers and materials using ultrasonic methods, unlike other elastomeric fibers.

Elastomeric polyolefin based yarns (e.g., lastol, Dow Chemical's XLA™) can be melt spun and subsequently processed into fabrics and other textile articles. It has been shown, as demonstrated in the examples below, that fibers of elastomeric propylene based polymer melt spun and wound without a finish applied cannot be removed from the spool. In most cases the fibers break because of the tackiness of one fiber overlaid on another. Thus, traditionally, a finish, usually a silicone-based finish, is applied to the surface of the fiber in order to be able to unwind the yarn after spinning and to reduce friction to facilitate knitting and other processes downstream from spinning. However, as discussed above, while facilitating unwinding, such finishes also introduce several disadvantages and must be removed in order for the fibers to be used in certain applications.

As described in greater detail below, the fibers of the present disclosure include anti-tack additives, e.g., anti-tacks from the family of bis-stearamides (fatty acid amides), talc, corn-starch, and $TiO_2$, where the additive can be admixed into the resin itself, melt spun and the resultant fiber on the spools is not tacky, and the fibers do not stick together. The anti-tack agent allows the individual fibers to be unwound without breaking without the need for a silicone-based finish. This allows for the elimination of silicone removal steps in apparel downstream processing, and enables gluing, or ultrasonic bonding for non-apparel applications such as diapers, narrows or the like.

Embodiments of the present disclosure include elastomeric propylene based polymer fibers that include an anti-tack agent incorporated into the fiber. The anti-tack agent can include compounds that provide an anti-tack benefit to the elastomeric propylene based polymer fiber such that the fiber may be used without the addition of a topical finish to the fiber, in particular without the use of a silicon-based finish. In addition, unlike most anti-tack compositions, the elastomeric fibers' inclusion of the anti-tack agent does not have a deleterious effect on the adhesion of the fiber or yarn, or to the desirable mechanical properties of the fiber or yarn, such as tenacity and elongation to break, and the like.

Elastomeric Propylene-Based Polymer

The elastomeric fiber of the present disclosure is made from an elastomeric propylene based polymer, as defined above. The elastomeric propylene based polymer can be a metallocene catalyzed propylene based elastomeric polymer. Exemplary commercially available elastomeric propylene based polymers suitable for use in preparing the fibers of the present disclosure include Vistamaxx™ 1100 and Vistamaxx™ 2100 by ExxonMobil Corporation. Additional elastomeric propylene-based polymers and compositions including these polypropylene-based fibers are described below.

The elastomeric yarns, filaments, and fibers in some aspects can be made from a composition including a blend of one or more elastomeric propylene-based polymers, one or more antioxidants, and one or more cross-linking agents (also referred to as coagents).

The terms "elastomeric propylene-based polymer," "propylene-based polymer," and "propylene polymer" are used interchangeably and include one or more elastomeric propylene-based polymers, one or more propylene-α-olefin copolymers, one or more propylene-α-olefin-diene terpolymers, and one or more propylene-diene copolymers. Blends of two or more of these polymers, copolymers and/or terpolymers are also included.

The term "elastomeric propylene-based polymer composition" refers to a composition including at least one elastomeric propylene-based polymer along with any additives which can be used to provide a melt spun filament or yarn.

The propylene-based polymer can be prepared by polymerizing propylene with one or more dienes. In at least one other specific embodiment, the propylene-based polymer can be prepared by polymerizing propylene with ethylene and/or at least one $C_4$-$C_{20}$ α-olefin, or a combination of ethylene and at least one $C_4$-$C_{20}$ α-olefin and one or more dienes. The one or more dienes can be conjugated or non-conjugated. Preferably, the one or more dienes are non-conjugated.

The comonomers can be linear or branched. Linear comonomers include ethylene or $C_4$-$C_8$ α-olefin, such as ethylene, 1-butene, 1-hexene, and 1-octene. Branched comonomers include 4-methyl-1-pentene, 3-methyl-1-pentene, and 3,5,5-trimethyl-1-hexene. In one or more embodiments, the comonomer can include styrene.

Illustrative dienes can include, but are not limited to, 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; vinyl norbornene (VNB); dicyclopendadiene (DCPD), and combinations thereof.

Suitable methods and catalysts for producing the propylene-based polymers are found in publications US 2004/0236042 and WO05/049672 and in U.S. Pat. No. 6,881,800, which are all incorporated by reference herein. Pyridine amine complexes, such as those described in WO03/040201 are also useful to produce the propylene-based polymers useful herein. The catalyst can involve a fluxional complex, which undergoes periodic intra-molecular re-arrangement so as to provide the desired interruption of stereo regularity as in U.S. Pat. No. 6,559,262, which is incorporated herein by reference. The catalyst can be a stereorigid complex with mixed influence on propylene insertion, see Rieger EP1070087, which is incorporated herein by reference. The catalyst described in EP1614699 could also be used for the production of backbones suitable for the embodiments of the present disclosure, which is incorporated herein by reference.

Polymerization methods for preparing the elastomeric propylene-based polymers include high pressure, slurry, gas, bulk, solution phase, and combinations thereof. Catalyst systems that can be used include traditional Ziegler-Natta catalysts and single-site metallocene catalyst systems. The catalyst used may have a high isospecificity. Polymerization may be carried out by a continuous or batch process and may include the use of chain transfer agents, scavengers, or other such additives well known to those skilled in the art. The polymers may also contain additives such as flow improvers, nucleators, and antioxidants which are normally added to improve or retain resin and/or yarn properties.

One suitable catalyst is a bulky ligand transition metal catalyst. The bulky ligand contains a multiplicity of bonded atoms, for example, carbon atoms, forming a group, which may be cyclic with one or more optional hetero-atoms. The bulky ligand may be metallocene-type cyclopentadienyl derivative, which can be mono- or poly-nuclear. One or more bulky ligands may be bonded to the transition metal atom. The bulky ligand is assumed, according to prevailing scientific theory, to remain in position in the course of polymerization to provide a homogenous polymerization effect. Other ligands may be bonded or coordinated to the transition metal, optionally detachable by a cocatalyst or activator, such as a hydrocarbyl or halogen-leaving group. It is assumed that detachment of any such ligand leads to the creation of a coordination site at which the olefin monomer can be inserted into the polymer chain. The transition metal atom is a Group IV, V or VI transition metal of the Periodic Table of Elements. One suitable transition metal atom is a Group IVB atom.

Suitable catalysts include single sited catalysts (SSC). These generally contain a transition metal of Groups 3 to 10 of the Periodic Table; and at least one ancillary ligand that remains bonded to the transition metal during polymerization. The transition metal may be used in a cationic state and stabilized by a cocatalyst or activator. Examples include metallocenes of Group 4 of the Periodic table such as titanium, hafnium or zirconium which are used in polymerization in the $d^0$ mono-valent cationic state and have one or two ancillary ligands as described in more detail hereafter. For coordination of polymerization, such catalysts may include features such as a ligand capable of abstraction and a ligand into which the ethylene (olefinic) group can be inserted.

The metallocene can be used with a cocatalyst, which may be alumoxane such as methylalumoxane having an average degree of oligomerization of about 4 to 30 as determined by vapor pressure osmometry. Alumoxane may be modified to provide solubility in linear alkanes or be used in a slurry but is generally used from a toluene solution. Such solutions may include unreacted trialkyl aluminum and the alumoxane concentration is generally indicated as mol Al per liter, which figure includes any trialkyl aluminum which has not so reacted to form an oligomer. The alumoxane, when used as cocatalyst, is generally used in molar excess, at a mol ratio of about 50 or more, including about 100 or more, about 1000 or less, and about 500 or less, relative to the transition metal.

The SSC may be selected from among a broad range, of available SSC's, to suit the type of polymer being made and the process window associated therewith in such a way that the polymer is produced under the process conditions at an activity of at least about 40,000 gram polymer per gram SSC (such as a metallocene), such as at least about 60,000 including in excess of about 100,000 gram polymer per gram SSC. By enabling the different polymers to be produced in different operating windows with an optimized catalyst selection, the SSC and any ancillary catalyst components can be used in small quantities, with optionally also using small amounts of scavengers. A catalyst killer can be used in equally small amounts and the various cost-effective methods can then be introduced to allow the non-polar solvent to be recycled and subjected to treatment to remove polar contaminants before re-use in the polymerization reactor(s).

The metallocene may be also be used with a cocatalyst that is a non- or weakly coordinated anion (the term non-coordinating anion as used herein includes weakly coordinated anions). The coordination should be sufficiently weak in any event, as evidenced by the progress of polymerization, to permit the insertion of the unsaturated monomer component. The non-coordinating anion may be supplied and reacted with the metallocene in any of the manners described in the art.

The precursor for the non-coordinating anion may be used with a metallocene supplied in a reduced valency state. The precursor may undergo a redox reaction. The precursor may be an ion pair of which the precursor cation is neutralized and/or eliminated in some manner. The precursor cation may be an ammonium salt. The precursor cation may be a triphenylcarbonium derivative.

The non-coordinating anion can be a halogenated, tetraaryl-substituted Group 10-14 non-carbon element-based anion, especially those that are have fluorine groups substituted for hydrogen atoms on the aryl groups, or on alkyl substituents on those aryl groups.

Effective Group 10-14 element cocatalyst complexes may be derived from an ionic salt including a 4-coordinate Group 10-14 element anionic complex, where $A^-$ can be represented as $$[(M)Q_1Q_2 \ldots Q_i]^-$$

where M is one or more Group 10-14 metalloid or metal, such as boron or aluminum, and each Q is a ligand effective for providing electronic or steric effects rendering $[(M')Q_1Q_2 \ldots Q_i]^-$ suitable as a non-coordinating anion as that is understood in the art, or a sufficient number of Q are such that $[(M') Q_1Q_2 \ldots Q Q_i]^-$ as a whole is an effective non-coordinating or weakly coordinating anion. Exemplary Q substituents specifically include fluorinated aryl groups, such as perfluorinated aryl groups, and include substituted Q groups having substituents additional to the fluorine substitution, such as fluorinated hydrocarbyl groups. Exemplary fluorinated aryl groups include phenyl, biphenyl, naphthyl and derivatives thereof.

The non-coordinating anion may be used in approximately equimolar amounts relative to the transition metal component, such as at least about 0.25, including about 0.5 and about 0.8 and no more than about 4, or about 2 or about 1.5.

Representative metallocene compounds can have the formula:

$$L^A L^B L^C_i MDE$$

where, $L^A$ is a substituted cyclopentadienyl or heterocyclopentadienyl ancillary ligand π-bonded to M; $L^B$ is a member of the class of ancillary ligands defined for $L^A$, or is J, a hetero-atom ancillary ligand σ-bonded to M; the $L^A$ and $L^B$ ligands may be covalently bridged together through a Group 14 element linking group; $L^C_i$ is an optional neutral, non-oxidizing ligand having a dative bond to M (i equals 0 to 3); M is a Group 4 or 5 transition metal; and, D and E are independently mono-anionic labile ligands, each having a a-bond to M, optionally bridged to each other or $L^A$ or $L^B$. The mono-anionic ligands are displaceable by a suitable activator to permit insertion of a polymerizable monomer or macro-monomer can insert for coordination polymerization on the vacant coordination site of the transition metal component.

Representative non-metallocene transition metal compounds usable as SSC's also include tetrabenzyl zirconium, tetra bis(trimethylsiylmethyl) zirconium, oxotris (trimethlsilylmethyl) vanadium, tetrabenzyl hafnium, tetrabenzyl titanium, bis(hexamethyl disilazido)dimethyl titanium, tris (trimethyl silyl methyl) niobium dichloride, and tris(trimethylsilylmethyl) tantalum dichloride.

Additional organometallic transition metal compounds suitable as olefin polymerization catalysts in accordance with the invention will be any of those Group 3-10 that can be converted by ligand abstraction into a catalytically active cation and stabilized in that active electronic state by a non-coordinating or weakly coordinating anion sufficiently labile to be displaced by an olefinically unsaturated monomer such as ethylene.

Other useful catalysts include metallocenes which are biscyclopentadienyl derivatives of a Group IV transition metal, such as zirconium or hafnium. These may be derivatives containing a fluorenyl ligand and a cyclopentadienyl ligand connected by a single carbon and silicon atom. The Cp ring may be unsubstituted and/or the bridge contains alkyl substituents, suitably alkylsilyl substituents to assist in the alkane solubility of the metallocene such as those disclosed in PCT published applications WO00/24792 and WO00/24793, each of which are incorporated herein by reference. Other possible metallocenes include those in PCT published application WO01/58912, which is incorporated herein by reference.

Other suitable metallocenes may be bisfluorenyl derivatives or unbridged indenyl derivatives which may be substituted at one or more positions on the fused ring with moieties which have the effect of increasing the molecular weight and so indirectly permit polymerization at higher temperatures.

The total catalyst system may additionally include one or more organometallic compounds as scavenger. Such compounds are meant to include those compounds effective for removing polar impurities from the reaction environment and for increasing catalyst activity. Impurities can be inadvertently introduced with any of the polymerization reaction components, particularly with solvent, monomer and catalyst feed, and adversely affect catalyst activity and stability. It can result in decreasing or even elimination of catalytic activity, particularly when ionizing anion pre-cursors activate the catalyst system. The impurities, or catalyst poisons include water, oxygen, polar organic compounds, metal impurities, etc. Steps can be taken to remove these poisons before introduction of such into the reaction vessel, for example, by chemical treatment or careful separation techniques after or during the synthesis or preparation of the various components, but some minor amounts of organometallic compound will still normally be used in the polymerization process itself.

Typically organometallic compounds can include the Group-13 organometallic compounds disclosed in U.S. Pat. Nos. 5,153,157 and 5,241,025 and PCT publications WO91/09882, WO94/03506, WO93/14132, and WO95/07941, each of which is incorporated herein by reference. Suitable compounds include triethyl aluminum, triethyl borane, triisobutyl aluminum, tri-n-octyl aluminum, methylalumoxane, and isobutyl alumoxane. Alumoxane also may be used in scavenging amounts with other means of activation, e.g., methylalumoxane and tri-isobutylaluminoxane with boron-based activators. The amount of such compounds to be used with catalyst compounds is minimized during polymerization reactions to that amount effective to enhance activity (and with that amount necessary for activation of the catalyst compounds If used in a dual role) since excess amounts may act as catalyst poisons.

The propylene-based polymer can have an average propylene content on a weight percent basis of about 60 wt % to about 99.7 wt %, including about 60 wt % to about 99.5 wt %, about 60 wt % to about 97 wt % and about 60 wt % to about 95 wt %, based on the weight of the polymer. In one aspect, the balance may include one or more other α-olefins or one or more dienes. In an embodiment, the content can be about 80 wt % to about 95 wt % propylene, about 83 wt % to about 95 wt % propylene, about 84 wt % to about 95 wt % propylene, and about 84 wt % to about 94 wt %, propylene based on the weight of the polymer. The balance of the propylene-based polymer optionally comprises a diene and/or one or more α-olefins. The α-olefin may include ethylene, butene, hexene or octene. When two α-olefins are present, they may include any combination such as ethylene and one of butene, hexene or octene. The propylene-based polymer comprises about 0.2 wt % to about 24 wt %, of a non-conjugated diene based on the weight of the polymer, including about 0.5 wt % to about 12 wt %, about 0.6 wt % to about 8 wt %, and about 0.7 wt % to about 5 wt %. In other embodiments, the diene content can be about 0.2 wt % to about 10 wt %, including about 0.2 to about 5 wt %, about 0.2 wt % to about 4 wt %, about 0.2 wt % to about 3.5 wt %, about 0.2 wt % to about 3.0 wt %, and about 0.2 wt % to about 2.5 wt % based on the weight of the polymer. In one or more embodiments above or elsewhere herein, the propylene-based polymer comprises ENB in an amount of about 0.5 to about 4 wt %, including about 0.5 to about 2.5 wt %, and 0.5 to about 2.0 wt %.

In other embodiments, the propylene-based polymer includes propylene and diene in one or more of the ranges described above with the balance comprising one or more $C_2$ and/or $C_4$-$C_{20}$ α-olefins. In general, this will amount to the propylene-based polymer including about 5 to about 40 wt % of one or more $C_2$ and/or $C_4$-$C_{20}$ α-olefins based the weight of the polymer. When $C_2$ and/or a $C_4$-$C_{20}$ α-olefins are present the combined amounts of these olefins in the polymer may be about 5 wt % or greater and falling within the ranges described herein. Other suitable ranges for the one or more α-olefins include about 5 wt % to about 35 wt %, including about 5 wt % to about 30 wt %, about 5 wt % to about 25 wt %, about 5 wt % to about 20 wt %, about 5 to about 17 wt % and about 5 wt % to about 16 wt %.

The propylene-based polymer can have a weight average molecular weight (Mw) of about 5,000,000 or less, a number average molecular weight (Mn) of about 3,000,000 or less, a z-average molecular weight (Mz) of about 10,000,000 or less, and a g' index of about 0.95 or greater measured at the weight average molecular weight (Mw) of the polymer using isotactic polypropylene as the baseline, all of which can be determined by size exclusion chromatography, e.g., 3D SEC, also referred to as GPC-3D as described herein.

In one or more embodiments above or elsewhere herein, the propylene-based polymer can have a Mw of about 5,000 to about 5,000,000 g/mole, including a Mw of about 10,000 to about 1,000,000, a Mw of about 20,000 to about 500,000 and a Mw of about 50,000 to about 400,000, wherein Mw is determined as described herein.

In one or more embodiments above or elsewhere herein, the propylene-based polymer can have a Mn of about 2,500 to about 2,500,000 g/mole, including a Mn of about 5,000 to about 500,000, a Mn of about 10,000 to about 250,000, and a Mn of about 25,000 to about 200,000, wherein Mn is determined as described herein.

In one or more embodiments above or elsewhere herein, the propylene-based polymer can have a Mz of about 10,000 to about 7,000,000 g/mole, including a Mz of about 50,000 to about 1,000,000, a Mz of about 80,000 to about 700,000, and a Mz of about 100,000 to about 500,000, wherein Mz is determined as described herein.

The molecular weight distribution index (MWD=(Mw/Mn)), sometimes referred to as a "polydispersity index" (PDI), of the propylene-based polymer can be about 1.5 to 40. The MWD can have an upper limit of about 40, or about 20, or about 10, or about 5, or about 4.5, and a lower limit of about 1.5, or about 1.8, or about 2.0. The MWD of the propylene-based polymer may be about 1.8 to about 5 and including about 1.8 to about 3. Techniques for determining the molecular weight (Mn and Mw) and molecular weight distribution (MWD) are well known in the art and can be found in U.S. Pat. No. 4,540,753 (which is incorporated by reference herein for purposes of U.S. practices) and references cited therein, in Macromolecules, 1988, volume 21, p 3360 (Verstrate et al.), and in accordance with the procedures disclosed in U.S. Pat. No. 6,525,157, column 5, lines 1-44, all of which are hereby incorporated by reference in their entirety.

The propylene-based polymer can have a g' index value of about 0.95 or greater, including about 0.98 or greater and about 0.99 or greater wherein g' is measured at the Mw of the polymer using the intrinsic viscosity of isotactic polypropylene as the baseline. For use herein, the g' index is defined as:

$$g' = \eta_b / \eta_l$$

where $\eta_b$ is the intrinsic viscosity of the propylene-based polymer and $\eta_l$ is the intrinsic viscosity of a linear polymer of the same viscosity-averaged molecular weight ($M_v$) as the propylene-based polymer. $\eta_l = K M_v^\alpha$, K and α were measured values for linear polymers and should be obtained on the same instrument as the one used for the g' index measurement.

The propylene-based polymer can have a density of about 0.85 g/cm$^3$ to about 0.92 g/cm$^3$, including from about 0.87 g/cm$^3$ to about 0.90 g/cm$^3$ and about 0.88 g/cm$^3$ to about 0.89 g/cm$^3$ at about room temperature as measured per the ASTM D-1505 test method.

The propylene-based polymer can have a melt flow rate MFR, about 2.16 kg weight (230° C.), equal to or greater than about 0.2 g/10 min as measured according to the ASTM D-I 238(A) test method as modified (described below). The MFR (2.16 kg (230° C.) may be about 0.5 g/10 min to about 200 g/10 min including from about 1 g/10 min to about 100 g/10 min. The propylene-based polymer may have an MFR of about 0.5 g/10 min to about 200 g/10 min, including about 2 g/10 min to about 30 g/10 min, about 5 g/10 min to about 30 g/10 min, about 10 g/10 min to about 30 g/10 min, about 10 g/10 min to about 25 g/10 min, and about 2 g/10 min to about 10 g/10 min.

The propylene-based polymer can have a Mooney viscosity ML (1+4) about 125° C., as determined according to ASTM D1646, of less than 100, such as less than about 75, including less than about 60 and less than about 30.

The propylene-based polymer can have a heat of fusion (Hf) determined according to the DSC procedure described later, which is greater than or equal to about 0.5 Joules per gram (J/g), and can be about 80 J/g, including about 75 J/g, about 70 J/g, about 60 J/g, about 50 J/g, and about 35 J/g. The propylene-based polymer may have a heat of fusion that is greater than or equal to about 1 J/g, including greater than or equal to about 5 J/g. In another embodiment, the propylene-based polymer can have a heat of fusion (Hf), which can be about 0.5 J/g to about 75 J/g, including about 1 J/g to about 75 J/g and about 0.5 J/g to about 35 J/g.

Suitable propylene-based polymers and compositions can be characterized in terms of both their melting points (Tm) and heats of fusion, which properties can be influenced by the presence of comonomers or steric irregularities that hinder the formation of crystallites by the polymer chains. In one or more embodiments, the heat of fusion can have a lower limit of about 1.0 J/g, or about 1.5 J/g, or about 3.0 J/g, or about 4.0 J/g, or about 6.0 J/g, or about 7.0 J/g, to an upper limit of about 30 J/g, or about 35 J/g, or about 40 J/g, or about 50 J/g, or about 60 J/g or about 70 J/g, or about 75 J/g, or about 80 J/g.

The crystallinity of the propylene-based polymer can also be expressed in terms of percentage of crystallinity (i.e., % crystallinity). In one or more embodiments above or elsewhere herein, the propylene-based polymer has a % crystallinity of about 0.5% to 40%, including about 1% to 30% and about 5% to 25% wherein % crystallinity is determined according to the DSC procedure described below. In another embodiment, the propylene-based polymer may have a crystallinity of less than about 40%, including about 0.25% to about 25%, from about 0.5% to about 22%, and from about 0.5% to about 20%. As disclosed above, the thermal energy for the highest order of polypropylene is estimated at about 189 J/g (i.e., 100% crystallinity is equal to 209 J/g.).

In addition to this level of crystallinity, the propylene-based polymer may have a single broad melting transition. Also, the propylene-based polymer can show secondary melting peaks adjacent to the principal peak, but for purposes herein, such secondary melting peaks are considered together as a single melting point, with the highest of these peaks (relative to baseline as described herein) being considered the melting point of the propylene-based polymer.

The propylene-based polymer may have a melting point (measured by DSC) of equal to or less than about 100° C., including less than about 90° C., less than about 80° C., and less than or equal to about 75° C., including the range from about 25° C. to about 80° C., about 25° C. to about 75° C., and about 30° C. to about 65° C.

The Differential Scanning calorimetry (DSC) procedure can be used to determine heat of fusion and melting temperature of the propylene-based polymer. The method is as follows: about 0.5 grams of polymer is weighed out and pressed to a thickness of about 15-20 mils (about 381-508 microns) at about 140° C.-150° C., using a "DSC mold" and Mylar™ polyester film as a backing sheet. The pressed pad is allowed to cool to ambient temperature by hanging in air (the Mylar is not removed). The pressed pad is annealed at room temperature (about 23-25° C.) for about 8 days. At the end of this period, an about 15-20 mg disc is removed from the pressed pad using a punch die and is placed in a 10 microliter aluminum sample pan. The sample is placed in a Differential Scanning calorimeter (Perkin Elmer Pyris 1 Thermal Analysis System) and is cooled to about −100° C. The sample is heated at 10° C./min to attain a final temperature of about 165° C. The thermal output, recorded as the area under the melting peak of the sample, is a measure of the heat of fusion and can be expressed in Joules per gram of polymer and is automatically calculated by the Perkin Elmer System. The melting point is recorded as the temperature of the greatest heat absorption within the range of melting of the sample relative to a baseline measurement for the increasing heat capacity of the polymer as a function of temperature.

The propylene-based polymer can have a triad tacticity of three propylene units, as measured by 13C NMR of about 75% or greater, about 80% or greater, about 82% or greater, about 85% or greater, or about 90% or greater. In an embodiment, the triad tacticty can be about 50 to about 99%, about 60 to about 99%, about 75 to about 99%, about 80 to about 99%; and in other embodiments about 60 to about 97%. Triad tacticity is well-known in the art and may be determined by the methods described in U.S. Patent Application Publication No. 2004/0236042, which is incorporated herein by reference.

The propylene-based polymer can be a blend of discrete random propylene-based polymers. Such blends can also include ethylene-based polymers and propylene-based polymers, or at least one of each such ethylene-based polymers and propylene-based polymers. The number of propylene based polymers can be three or less, including two or less.

The elastomeric propylene-based polymer can include a blend of two propylene-based polymers differing in the olefin content, the diene content, or both.

In one or more embodiments above or elsewhere herein, the propylene-based polymer can include a propylene based elastomeric polymer produced by random polymerization processes leading to polymers having randomly distributed irregularities in stereoregular propylene propagation. This is in contrast to block copolymers in which constituent parts of the same polymer chains are separately and sequentially polymerized.

The propylene-based polymers can also include copolymers prepared according the procedures in WO 02/36651, which is incorporated herein by reference. Likewise, the propylene-based polymer can include polymers consistent with those described in WO 03/040202, WO 03/040201, WO 03/040095, WO 03/040201, WO 03/040233, and/or WO 03/040442, which is incorporated herein by reference. Additionally, the propylene-based polymer can include polymers consistent with those described in EP 1 233 191, and U.S. Pat. No. 6,525,157, along with suitable propylene homo- and copolymers described in U.S. Pat. No. 6,770,713 and U.S. Patent Application Publication 2005/215964, all of which are incorporated by reference. The propylene-based polymer can also include one or more polymers consistent with those described in EP 1 614 699 or EP 1 017 729, each of which is incorporated herein by reference.

Grafted (Functionalized) Backbone

In one or more embodiments, the propylene-based polymer can be grafted (i.e. "functionalized") using one or more grafting monomers. As used herein, the term "grafting" denotes covalent bonding of the grafting monomer to a polymer chain of the propylene-based polymer.

The grafting monomer can be or include at least one ethylenically unsaturated carboxylic acid or acid derivative, such as an acid anhydride, ester, salt, amide, imide, and acrylates, among others. Illustrative monomers include, but are not limited to, acrylic acid, methacrylic acid, maleic acid, fumaric acid, itaconic acid, citraconic acid, mesaconic acid, maleic anhydride, 4-methyl cyclohexene-1,2-dicarboxylic acid anhydride, bicyclo(2,2,2)octene-2,3-dicarboxylic acid anhydride, 1,2,3,4,5,8,9,10-octahydronaphthalene-2,3-dicarboxylic acid anhydride, 2-oxa-1,3-diketospiro(4,4)nonene, bicycle (2,2,1)heptene-2,3-dicarboxylic acid anhydride, maleopimaric acid, tetrahydrophthalic anhydride, norbornene-2,3-dicarboxylic acid anhydride, nadic anhydride, methyl nadic anhydride, himic anhydride, methyl himic anhydride, and 5-methylbicyclo(2,2,1)heptene-2,3-dicarboxylic acid anhydride. Other suitable grafting monomers include methyl acrylate and higher alkyl acrylates, methyl methacrylate and higher alkyl methacrylates, acrylic acid, methacrylic acid, hydroxy-methyl methacrylate, hydroxyl- ethyl methacrylate and higher hydroxy-alkyl methacrylates and glycidyl methacrylate. Maleic anhydride is a preferred grafting monomer.

In one or more embodiments, the grafted propylene based polymer comprises about 0.5 to about 10 wt % ethylenically unsaturated carboxylic acid or acid derivative, including about 0.5 to about 6 wt %, about 0.5 to about 3 wt %; in other embodiments about 1 to about 6 wt %, and about 1 to about 3 wt %. Where the graft monomer is maleic anhydride, the maleic anhydride concentration in the grafted polymer may be about 1 to about 6 wt %, including about 0.5 wt % or about 1.5 wt % as a minimum.

Styrene and derivatives thereof such as paramethyl styrene, or other higher alkyl substituted styrenes such as t-butyl styrene can be used as a charge transfer agent in presence of the grafting monomer to inhibit chain scissioning. This allows further minimization of the beta scission reaction and the production of a higher molecular weight grafted polymer (MFR=1.5).

Preparing Grafted Propylene-Based Polymers

A grafted propylene-based polymer can be prepared using conventional techniques. For example, the graft polymer can be prepared in solution, in a fluidized bed reactor, or by melt grafting. A grafted polymer can be prepared by melt blending in a shear-imparting reactor, such as an extruder reactor. Single screw or twin screw extruder reactors such as co-rotating intermeshing extruder or counter-rotating non-intermeshing extruders but also co-kneaders such as those sold by Buss are useful for this purpose.

The grafted polymer can be prepared by melt blending an ungrafted propylene-based polymer with a free radical generating catalyst, such as a peroxide initiator, in the presence of a grafting monomer. One suitable sequence for the grafting reaction includes melting the propylene-based polymer, adding and dispersing the grafting monomer, introducing peroxide and venting the unreacted monomer and by-products resulting from the peroxide decomposition. Other sequences can include feeding the monomers and the peroxide pre-dissolved in a solvent.

Illustrative peroxide initiators include but are not limited to: diacyl peroxides such as benzoyl peroxide; peroxyesters such as tert-butylperoxy benzoate, tert-butylperoxy acetate, O—O-tert-butyl-O-(2-ethylhexyl)monoperoxy carbonate; peroxyketals such as n-butyl-4,4-di-(tert-butyl peroxy) valerate; and dialkyl peroxides such as 1,1-bis(tertbutylperoxy) cyclohexane, 1,1-bis(tert-butylperoxy)-3,3,5-trimethylcyclohexane, 2,2-bis(tert-butylperoxy)butane, dicumylperoxide, tert-butylcumylperoxide, di-(2-tert-butylperoxyisopropyl-(2))benzene, di-tert-butylperoxide (DTBP), 2,5-dimethyl-2,5-di(tert-butylperoxy)hexane, 2,5-dimethyl-2,5-di(tert-butylperoxy)hexyne, 3,3,5,7,7-pentamethyl 1,2,4-trioxepane, among others and combinations thereof.

Polyolefinic Thermoplastic Resin

The term "polyolefinic thermoplastic resin" as used herein refers to any material that is not a "rubber" and that is a polymer or polymer blend having a melting point of 70° C., or more and considered by persons skilled in the art as being thermoplastic in nature, e.g., a polymer that softens when exposed to heat and returns to its original condition when cooled to room temperature. The polyolefinic thermoplastic resin can contain one or more polyolefins, including polyolefin homopolymers and polyolefin copolymers. Except as stated otherwise, the term "copolymer" means a polymer derived from two or more monomers (including terpolymers, tetrapolymers, etc.), and the term "polymer" refers to any carbon-containing compound having repeat units from one or more different monomers.

Illustrative polyolefins can be prepared from monoolefin monomers including, but are not limited to, monomers having 2 to 7 carbon atoms, such as ethylene, propylene, 1-butene, isobutylene, 1-pentene, 1-hexene, 1-octene, 3-methyl-1-pentene, 4-methyl-1-pentene, 5-methyl-1-hexene, mixtures thereof and copolymers thereof with (meth) acrylates and/or vinyl acetates. The polyolefinic thermoplastic resin component is unvulcanized or non crosslinked.

The polyolefinic thermoplastic resin may contain polypropylene. The term "polypropylene" as used herein broadly means any polymer that is considered a "polypropylene" by persons skilled in the art and includes homo, impact, and random polymers of propylene. The polypropylene used in the compositions described herein has a melting point above about 110° C., includes at least about 90 wt % propylene units, and contains isotactic sequences of those units. The polypropylene can also include atactic sequences or s syndiotactic sequences, or both. The polypropylene can also include essentially syndiotactic sequences such that the melting point of the polypropylene is above about 110° C. The polypropylene can either derive exclusively from propylene monomers (i.e., having only propylene units) or derive from mainly propylene (more than about 80% propylene) with the remainder derived from olefins, such as ethylene, and/or $C_4$-$C_{10}$ α-olefins. Certain polypropylenes have a high MFR (e.g., from a low of about 10, or about 15, or about 20 g/10 min to a high of about 25 or about 30 g/10 min.) Others have a lower MFR, e.g., "fractional" polypropylenes which have an MFR less than about 1.0. Those with high MFR can be useful for ease of processing or compounding.

A polyolefinic thermoplastic resin may be or include isotactic polypropylene. The polyolefinic thermoplastic resin may contain one or more crystalline propylene homopolymers or copolymers of propylene having a melting temperature greater than about 105° C. as measured by DSC. Exemplary copolymers of propylene include, but are not limited to, terpolymers of propylene, impact copolymers of propylene, random polypropylene and mixtures thereof. The comonomers may have 2 carbon atoms, or 4 to 12 carbon atoms, such as ethylene. Such polyolefinic thermoplastic resin and methods for making the same are described in U.S. Pat. No. 6,342,565, which is incorporated herein by reference.

The term "random polypropylene" as used herein broadly means a copolymer of propylene having up to about 9 wt %, such as about 2 wt % to 8 wt % of an alpha olefin comonomer. An α-olefin comonomer may have 2 carbon atoms, or 4 to 12 carbon atoms.

A random polypropylene may have a 1% secant modulus of about 100 kPsi to about 200 kPsi, as measured according to ASTM D790A. The 1% secant modulus can be about 140 kPsi to 170 kPsi, as measured according to ASTM D790A, including about 140 kPsi to 160 kPsi or having a low of about 100, about 110, or about 125 kPsi to a high of about 145, about 160, or about 175 kPsi, as measured according to ASTM D790A.

Random polypropylene can have a density of about 0.85 to about 0.95 g/cm$^3$, as measured by ASTM D79, including a density of about 0.89 g/cm$^3$ to about 0.92 g/cm$^3$, or having a low of about 0.85, about 0.87, or about 0.89 g/cm$^3$ to a high of about 0.90, about 0.91, about 0.92 g/cm$^3$, as measured by ASTM D792.

Additional Elastomeric Component

The elastomeric polypropylene-based polymer composition can optionally include one or more additional elastomeric components. The additional elastomeric component can be or include one or more ethylene-propylene copolymers (EP). The ethylene-propylene polymer (EP) is non-crystalline, e.g., atactic or amorphous, but the EP may be crystalline (including "semi-crystalline"). The crystallinity of the EP may be derived from the ethylene, which can be determined by a number of published methods, procedures and techniques. The crystallinity of the EP can be distinguished from the crystallinity of the propylene-based polymer by removing the EP from the composition and then measuring the crystallinity of the residual propylene-based polymer. Such crystallinity measured is usually calibrated using the crystallinity of polyethylene and related to the comonomer content. The percent crystallinity in such cases is measured as a percentage of polyethylene crystallinity and thus the origin of the crystallinity from ethylene is established.

In one or more embodiments, the EP can include one or more optional polyenes, including particularly a diene; thus, the EP can be an ethylene-propylene-diene (commonly called "EPDM"). The optional polyene is considered to be any hydrocarbon structure having at least two unsaturated bonds wherein at least one of the unsaturated bonds is readily incorporated into a polymer. The second bond may partially take part in polymerization to form long chain branches but preferably provides at least some unsaturated bonds suitable for subsequent curing or vulcanization inpost polymerization processes. Examples of EP or EPDM copolymers include V722, V3708P, MDV 91-9, V878 that are commercially available under the trade name VISTALON from ExxonMobil Chemicals. Several commercial EPDM are available from Dow under the trade names Nordel IP and MG grades.). Certain rubber components (e.g., EPDMs, such as VISTALON 3666 from ExxonMobil Chemical) include additive oil that is preblended before the rubber component is combined with the thermoplastic. The type of additive oil utilized will be that customarily used in conjunction with a particular rubber component.

Examples of the optional polyenes include, but are not limited to, butadiene, pentadiene, hexadiene (e.g., 1,4-hexadiene), heptadiene (e.g., 1,6-heptadiene), octadiene (e.g., 1,7-octadiene), nonadiene (e.g., 1,8-nonadiene), decadiene (e.g., 1,9-decadiene), undecadiene (e.g., 1,10-undecadiene), dodecadiene (e.g., 1,11-dodecadiene), tridecadiene (e.g., 1,12-tridecadiene), tetradecadiene (e.g., 1,13-tetradecadiene), pentadecadiene, hexadecadiene, heptadecadiene, octadecadiene, nonadecadiene, icosadiene, heneicosadiene, docosadiene, tricosadiene, tetracosadiene, pentacosadiene, hexacosadiene, heptacosadiene, octacosadiene, nonacosadiene, triacontadiene, and polybutadienes having a molecular weight (Mw) of less than 1000 g/mol. Examples of straight chain acyclic dienes include, but are not limited to 1,4-hexadiene and 1,6-octadiene. Examples of branched chain acyclic dienes include, but are not limited to 5-methyl-1,4-hexadiene, 3,7-dimethyl-1,6-octadiene, and 3,7-dimethyl-1,7-octadiene. Examples of single ring alicyclic dienes include, but are not limited to 1,4-cyclohexadiene, 1,5-cyclooctadiene, and 1,7-cyclododecadiene. Examples of multi-ring alicyclic fused and bridged ring dienes include, but are not limited to, tetrahydroindene; norbornadiene; methyltetrahydroindene; dicyclopentadiene; bicyclo(2.2.1) hepta-2,5-diene; and alkenyl-, alkylidene-, cycloalkenyl-, and cyloalkyliene norbornenes [including, e.g., 5-methylene-2-norbornene, 5-ethylidene-2-norbornene, 5-propenyl-2-norbornene, 5-isopropylidene-2-norbornene, 5-(4-cyclopentenyl)-2-norbornene, 5-cyclohexylidene-2-norbornene, and 5-vinyl-2-norbornene]. Examples of cycloalkenyl-substituted alkenes include, but are not limited to, vinyl cyclohexene, ally cyclohexene, vinylcyclooctene, 4-inylcyclohexene, allyl cyclodecene, vinylcyclododecene, and tetracyclododecadiene.

In another embodiment, the additional elastomeric component can include, but is not limited to, styrene/butadiene rubber (SBR), styrene/isoprene rubber (SIR), styrene/isoprene/butadiene rubber (SIBR), styrene-butadiene-styrene block copolymer (SBS), hydrogenated styrenebutadiene-styrene block copolymer (SEBS), hydrogenated styrene-butadiene block copolymer (SEB), styrene-isoprenestyrene block copolymer (SIS), styrene-isoprene block copolymer (SI), hydrogenated styrene-isoprene block copolymer (SEP), hydrogenated styrene-isoprene-styrene block copolymer (SEPS), styrene-ethylene/butylene-ethylene block copolymer (SEBE), styrene-ethylene-styrene block copolymer (SES), ethylene-ethylene/butylene block copolymer (EEB), ethylene-ethylene/butylene/styrene block copolymer (hydrogenated BR-SBR block copolymer), styrene-ethylene/butylene-ethylene block copolymer (SEBE), ethylene-ethylene/butylene-ethylene block copolymer (EEBE), polyisoprene rubber, polybutadiene rubber, isoprene butadiene rubber (IBR), polysulfide, nitrile rubber, propylene oxide polymers, star-branched butyl rubber and halogenated star-branched butyl rubber, brominated butyl rubber, chlorinated butyl rubber, star-branched polyisobutylene rubber, star-branched brominated butyl(polyisobutylene/isoprene copolymer) rubber; poly(isobutylene-co-alkylstyrene), suitable isobutylene/methylstyrene copolymers such as isobutylene/meta-bromomethylstyrene, isobutylene/bromomethylstyrene, isobutylene/chloromethylstyrene, halogenated isobutylene cyclopentadiene, and isobutylene/chloromethylstyrene and mixtures thereof. The additional elastomeric components include hydrogenated styrene-butadienestyrene block copolymer (SEBS), and hydrogenated styreneisoprene-styrene block copolymer (SEPS).

The additional elastomeric component can also be or include natural rubber. Natural rubbers are described in detail by Subramaniam in RUBBER TECHNOLOGY 179-208 (1995). Suitable natural rubbers can be selected from the group consisting of Malaysian rubber such as SMR CV, SMR 5, SMR 10, SMR 20, and SMR 50 and mixtures thereof, wherein the natural rubbers have a Mooney viscosity at about 100° C. (ML 1+4) of about 30 to 120, including about 40 to 65. The Mooney viscosity test referred to herein is in accordance with ASTM D-1646.

The additional elastomeric component can also be or include one or more synthetic rubbers. Suitable commercially available synthetic rubbers include NATSYN™ (Goodyear Chemical Company), and BUDENE™ 1207 or BR 1207 (Goodyear Chemical Company). A suitable rubber is high cis-polybutadiene (cis-BR). By "cis-polybutadiene" or "high cis-polybutadiene", it is meant that 1,4-cis polybutadiene is used, wherein the amount of cis component is at least about 95%. An example of high cis-polybutadiene commercial products used in the composition BUDENE™ 1207.

The additional elastomeric component can be present up to about 50 phr (parts per hundred rubber), up to about 40 phr or up to about 30 phr. In one or more embodiments, the amount of the additional rubber component can have a low of about 1.7, or about 20 phr to a high of about 25, about 35, or about 50 phr.

Additive Oil

The elastomeric propylene-based polymer composition can optionally include one or more additive oils. Such "additive oils" should not be confused with "finishing oils" as used in the present disclosure. The "additive oils," as used herein, refer to such oils added during preparation of the elastomeric propylene based polymer, as opposed to a finishing oil, which, as defined above, is applied to the surface of a formed fiber. The term "additive oil" includes both "process oils" and "extender oils." For example, "additive oil" may include hydrocarbon oils and plasticizers, such as organic esters and synthetic plasticizers. Many additive oils are derived from petroleum fractions, and have particular ASTM designations depending on whether they fall into the class of paraffinic, naphthenic, or aromatic oils. Other types of additive oils include mineral oil, alpha olefinic synthetic oils, such as liquid polybutylene, e.g., products sold under the trademark Parapol®. Additive oils other than petroleum based oils can also be used, such as oils derived from coal tar and pine tar, as well as synthetic oils, e.g., polyolefin materials (e.g., SpectaSyn™ and Elevast™, both supplied by ExxonMobil Chemical Company.

It is well-known in the art which type of oil should be used with a particular rubber, as well as suitable amounts (quantity) of oil. The additive oil can be present in amounts of about 5 to about 300 parts by weight per 100 parts by weight of the blend of the rubber and thermoplastic components. The amount of additive oil may also be expressed as about 30 to 250 parts or about 70 to 200 parts by weight per 100 parts by weight of the rubber component. Alternatively, the quantity of additive oil can be based on the total rubber content, and defined as the ratio, by weight, of additive oil to total rubber and that amount may in certain cases be the combined amount of process oil and extender oil. The ratio may be, for example, about 0 to about 4.0/1. Other ranges, having any of the following lower and upper limits, may also be utilized: a lower limit of about 0.1/1, or about 0.6/1, or about 0.8/1, or about 1.0/1, or about 1.2/1, or about 1.5/1, or about 1.8/1, or about 2.0/1, or about 2.5/1; and an upper limit (which may be combined with any of the foregoing lower limits) of about 4.0/1, or about 3.8/1, or about 3.5/1, or about 3.2/1, or about 3.0/1, or about 2.8/1. Larger amounts of additive oil can be used, although the deficit is often reduced physical strength of the composition, or oil weeping, or both.

Polybutene oils are suitable. Exemplary polybutene oils have an Mn of less than about 15,000, and include homopolymer or copolymer of olefin derived units having 3 to 8 carbon atoms and more preferably 4 to 6 carbon atoms. The polybutene may be a homopolymer or copolymer of a $C_4$ raffinate. Exemplary low molecular weight polymers termed "polybutene" polymers is described in, for example, SYNTHETIC LUBRICANTS AND HIGH-PERFORMANCE FUNCTIONAL FLUIDS 357-392 (Leslie R. Rudnick & Ronald L. Shubkin, ed., Marcel Dekker 1999) (hereinafter "polybutene processing oil" or "polybutene").

The polybutene processing oil can be a copolymer having at least isobutylene derived units, and optionally 1-butene derived units, and/or 2-butene derived units. The polybutene can be a homopolymer if isobutylene, or a copolymer of isobutylene and 1-butene or 2-butene, or a terpolymer of isobutylene and 1-butene and 2-butene, wherein the isobutylene derived units are about 40 to 100 wt % of the copolymer, the 1-butene derived units are about 0 to 40 wt % of the copolymer, and the 2-butene derived units are about 0 to 40 wt % of the copolymer. The polybutene can be a copolymer or terpolymer wherein the isobutylene derived units are about 40 to 99 wt % of the copolymer, the 1-butene derived units are about 2 to 40 wt % of the copolymer, and the 2-butene derived units are about 0 to 30 wt % of the copolymer. The polybutene may also be a terpolymer of the three units, wherein the isobutylene derived units are about 40 to 96 wt % of the copolymer, the 1-butene derived units are about 2 to 40 wt % of the copolymer, and the 2-butene derived units are about 2 to 20 wt % of the copolymer. Another suitable polybutene is a homopolymer or copolymer of isobutylene and 1-butene, wherein the isobutylene derived units are about 65 to 100 wt % of the homopolymer or copolymer, and the 1-butene derived units are about 0 to 35 wt % of the copolymer. Commercial examples of a suitable processing oil includes the PARAPOL™ Series of processing oils or polybutene grades or Indopol™ from Soltex Synthetic Oils and Lubricants from BP/Innovene.

The processing oil or oils can be present at about 1 to 60 phr, including about 2 to 40 phr, about 4 to 35 phr and about 5 to 30 phr in yet another embodiment.

The processing oil or oils can also serve as a non-crystalline mobilizing additive, which helps prevent embrittlement of polyolefins and maintains their flexibility, particularly those that are subsequently subjected to irradiation to facilitate crosslinking (U.S. Pat. No. 4,110,185, which is incorporated herein by reference).

Cross-Linking Agents/Co-Agents

The elastomeric propylene-based polymer composition can optionally include one or more cross-linking agents, also referred to as co-agents. Suitable co-agents can include liquid and metallic multifunctional acrylates and methacrylates, functionalized polybutadiene resins, functionalized cyanurate, and allyl isocyanurate. More particularly, suitable coagents can include, but are not limited to polyfunctional vinyl or allyl compounds such as, for example, triallyl cyanurate, triallyl isocyanurate, pentaerthritol tetramethacrylate, ethylene glycol dimethacrylate, diallyl maleate, dipropargyl maleate, dipropargyl monoallyl cyanurate, azobisisobutyronitrile and the like, and combinations thereof. Commercially available cross-linking agents/co-agents can be purchased from Sartomer.

The elastomeric propylene-based polymer composition may contain about 0.1 wt % or greater of co-agent based on the total weight of polymer composition. The amount of co-agent(s) can be about 0.1 wt % to about 15 wt %, based on the total weight of polymer composition. In one or more embodiments, the amount of co-agent(s) can have a low of about 0.1 wt %, about 1.5 wt % or about 3.0 wt % to a high of about 4.0 wt %, about 7.0 wt %, or about 15 wt %, based on the total weight of blend. In one or more embodiments, the amount of co-agent (s) can have a low of about 2.0 wt %, about 3.0 wt % or about 5.0 wt % to a high of about 7.0 wt %, about 9.5 wt %, or about 12.5 wt %, based on the total weight of the polymer composition.

Antioxidants

The elastomeric propylene-based polymer composition can optionally include one or more anti-oxidants. Suitable anti-oxidants can include hindered phenols, phosphites, hindered amines, Irgafos 168, Irganox 1010, Irganox 3790, Irganox B225, Irganox 1035, Irgafos 126, Irgastab 410, Chimassorb 944, etc. made by Ciba Geigy Corp. These may be added to the elastomeric composition to protect against degradation during shaping or fabrication operation and/or to better control the extent of chain degradation which can be especially useful where the elastomeric propylene-based polymer composition is exposed to e-beam.

The elastomeric propylene-based composition can contain at least about 0.1 wt % of antioxidant, based on the total weight of blend. In one or more embodiments, the amount of antioxidant(s) can be about 0.1 wt % to about 5 wt %, based on the total weight of blend. In one or more embodiments, the amount of antioxidant(s) can have a low of about 0.1 wt %, about 0.2 wt % or about 0.3 wt % to a high of about 1 wt %, about 2.5 wt %, or about 5 wt %, based on the total weight of blend. In one or more embodiments, the amount of antioxidant(s) is about 0.1 wt %, based on the total weight of blend. In one or more embodiments, the amount of antioxidant(s) is about 0.2 wt %, based on the total weight of blend. In one or more embodiments, the amount of antioxidant(s) is about 0.3 wt %, based on the total weight of blend. In one or more embodiments, the amount of antioxidant(s) is about 0.4 wt %, based on the total weight of blend. In one or more embodiments, the amount of antioxidant(s) is about 0.5 wt %, based on the total weight of blend.

Blending and Additives

In one or more embodiments, the individual materials and components, such as the propylene-based polymer and optionally the one or more polyolefinic thermoplastic resins, additional elastomeric component, additive oil, coagents, and anti-oxidants can be blended by melt-mixing to form a blend. Examples of machinery capable of generating the shear and mixing include extruders with kneaders or mixing elements with one or more mixing tips or flights, extruders with one or more screws, extruders of co or counter rotating type, Banbury mixer, Farrell Continuous mixer, and the Buss Kneader. The type and intensity of mixing, temperature, and residence time required can be achieved by the choice of one of the above machines in combination with the selection of kneading or mixing elements, screw design, and screw speed (<3000 RPM).

In one or more embodiments, the blend can include the propylene-based polymer in an amount having a low of about 60, about 70 or about 75 wt % to a high of about 80, about 90, or about 95 wt %. In one or more embodiments, the blend can include the one or more polyolefinic thermoplastic components in an amount having a low of about 5, about 10, or about 20 wt % to a high of about 25, about 30, or about 75 wt %. In one or more embodiments, the blend can include the additional elastomeric component in an amount ranging from a low of about 5, about 10 or about 15 wt % to a high of about 20, about 35, or about 50 wt %.

In one or more embodiments, the co-agents, antioxidants, and/or other additives can be introduced at the same time as the other polymer components or later downstream in case of using an extruder or Buss kneader or only later in time. In addition to the co-agents and antioxidants described, other additives can include antiblocking agents, antistatic agents, ultraviolet stabilizers, foaming agents, and processing aids. The additives can be added to the blend in pure form or in master batches.

Cured Products

The formed article (e.g., extruded article) can be a fiber, yarn or film, and may be at least partially crosslinked or cured. Cross-linking provides the articles with heat resistance which is useful when the article, such as a fiber or yarn, will be exposed to higher temperatures. As used herein, the term "heat-resistant" refers to the ability of a polymer composition or an article formed from a polymer composition to pass the high temperature heat-setting and dyeing tests described herein.

As used herein, the terms "cured," "crosslinked," "at least partially cured," and "at least partially crosslinked" refer to a composition having at least 2 wt % insolubles based on the total weight of the composition. The elastomeric polypropylene-based compositions described herein can be cured to a degree so as to provide at least about 3 wt %, or at least about 5 wt %, or at least about 10 wt %, or at least about 20 wt %, or at least about 35 wt %, or at least about 45 wt %, or at least about 65 wt %, or at least about 75 wt %, or at least about 85 wt %, or less than about 95 wt % insolubles using Xylene as the solvent by Soxhlet extraction.

In a particular embodiment, the crosslinking is accomplished by electron beam or simply "e-beam" after shaping or extruding the article. Suitable e-beam equipment is available from E-BEAM Services, Inc. In a particular embodiment, electrons are employed at a dosage of about 100 kGy or less in multiple exposures. The source can be any electron beam generator operating in a range of about 150 Kev to about 12 mega-electron volts (MeV) with a power output capable of supplying the desired dosage. The electron voltage can be adjusted to appropriate levels which may be, for example, about 100,000; about 300,000; about 1,000,000; about 2,000,000; about 3,000,000; about 6,000,000. A wide range of apparatus for irradiating polymers and polymeric articles is available.

Effective irradiation is generally carried out at a dosage between about 10 kGy (Kilogray) to about 350 kGy, preferably from about 20 to about 350 kGy, or from about 30 to about 250 kGy, or from about 40 to about 200 kGy. In a particular aspect of this embodiment, the irradiation is carried out at room temperature and in air In another embodiment, crosslinking can be accomplished by exposure to one or more chemical agents in addition to the e-beam cure. Illustrative chemical agents include but are not limited to peroxides and other free radical generating agents, sulfur compounds, phenolic resins, and silicon hydrides. In a particular aspect of this embodiment, the crosslinking agent is either a fluid or is converted to a fluid such that it can be applied uniformly to the article. Fluid crosslinking agents include those compounds which are gases (e.g., sulfur dichloride), liquids (e.g., Trigonox C, available from Akzo Nobel), solutions (e.g., dicumyl peroxide in acetone, or suspensions thereof (e.g., a suspension or emulsion of dicumyl peroxide in water, or redox systems based on peroxides).

Illustrative peroxides include, but are not limited to dicumyl peroxide, di-tert-butyl peroxide, t-butyl perbenzoate, benzoyl peroxide, cumene hydroperoxide, t-butyl peroctoate, methyl ethyl ketone peroxide, 2,5-dimethyl-2,5-di(tbutyl peroxy)hexane, lauryl peroxide, tert-butyl peracetate. When used, peroxide curatives are generally selected from organic peroxides. Examples of organic peroxides include, but are not limited to, di-tert-butyl peroxide, dicumyl peroxide, t-butylcumyl peroxide, α,α-bis(tert-butylperoxy) diisopropyl benzene, 2,5 dimethyl 2,5-di(t-butylperoxy) hexane, 1,1-di(t-butylperoxy)-3,3,5-trimethyl cyclohexane, -butyl-4,4-bis(tert-butylperoxy) valerate, benzoyl peroxide, lauroyl peroxide, dilauroyl peroxide, 2,5-dimethyl-2,5-di(tert-butylperoxy) hexene-3, and mixtures thereof. Also, diaryl peroxides, ketone peroxides, peroxydicarbonates, peroxyesters, dialkyl peroxides, hydroperoxides, peroxyketals and mixtures thereof may be used.

In one or more embodiments, the crosslinking can be carried out using hydrosilylation techniques.

In one or more embodiments, the crosslinking can be carried out under an inert or oxygen-limited atmosphere. Suitable atmospheres can be provided by the use of helium, argon, nitrogen, carbon dioxide, xenon and/or a vacuum.

Crosslinking either by chemical agents or by irradiation can be promoted with a crosslinking catalyst, such as organic bases, carboxylic acids, and organometallic compounds including organic titanates and complexes or carboxylates of lead, cobalt, iron, nickel, zinc, and tin (such as dibutyltindilaurate, dioctyltinmaleate, dibutyltindiacetate, dibutyltindioctoate, stannous acetate, stannous octoate, lead naphthenate, zinc caprylate, cobalt naphthenate, and the like).

Thus, as described above, in some exemplary embodiments the elastomeric ethylene-propylene based polymer also includes a diene and/or a cross-linking agent. In embodiments, the diene is selected from the following: 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; vinyl norbornene (VNB); dicyclopendadiene (DCPD), and combinations thereof. In embodiments, the cross-linking agent is selected from the following: multifunctional acrylates, multifunctional methacrylates, functionalized polybutadiene resins, functionalized cyanurate, and allyl isocyanurate, and combinations thereof.

Anti-Tack Agents

The anti-tack agent of the present disclosure can include any anti-tack agent that, when incorporated into the fiber with the elastomeric polymer reduces the tackiness such that the fiber can be spun, wound and unwound from the package. Exemplary anti-tack agents include, but are not limited to anti-tacks from the group of anti-tacks called fatty acid amides or bis-stearamides (e.g., ethylene bis-stearamides, such as Ceridust® produced by Clariant Corporation); $TiO_2$; Advawax™ from Rohm and Hass (e.g., N,N'-ethylene bis-stearamide or mixed with metal stearates (depending on the grade). Acrawax™ from Lonza is N,N'-ethylene bisstearamide); cellulose acetate butyrate (CAB) and/or cellulose acetate propionate (CAP) (such as descried in U.S. Pat. No. 6,232,374, which is incorporated herein by reference); talc; starch, including corn starch; clays; metal salts of stearic acid, metal salts of oleic acid or palmitic, and the like, and combinations of one or more of the above. In embodiments, the anti-tack agent is a bis-stearamide, preferably an ethylene bis-stearamide, most preferably Ceridust® 3910 (e.g., bi-stearyl-ethylene-diamide; N,N'-ethylene bisstearamide; N,N'-ethylene bis(octadecanamide); and 1,2-bis(octadecanamido) ethane).

In an embodiment, the anti-tack may be a combination of a bis-stearamide anti-tack agent and another anti-tack agent, such as, but not limited to, $TiO_2$, talc, and corn starch. In embodiments, certain anti-tack agents may also act as fillers, such as for example, $TiO_2$, talc, and corn starch.

The anti-tack agents of the present disclosure are added to the elastomeric propylene based polymer composition in an amount sufficient to allow unwinding of the fibers from the package. In embodiments, about 0.5 to about 30% by weight of an anti-tack agent is added to the polymer composition. To some extent, the amount of anti-tack agent used in a particular embodiment will depend on the type of anti-tack agent used. For instance, bis-stearamide anti-tack agents, such as Ceridust® 3910, are effective in low amounts, and they are expensive, so a smaller amount is desirable. Thus, when using bis-stearamide type anti-tack agents, preferably about 0.5 to about 10 wt % of anti-tack is used, though more could be used, and this range is not intended to be limiting. However, when using less expensive materials, particularly materials that may also act as filler materials, it is advantageous to use as much of the anti-tack/filler material that will both provide anti-tack properties without negatively affecting the fiber properties. For example, in an exemplary embodiment, the anti-tack may be $TiO_2$, talc, corn starch, or similar material, or a combination thereof, in an amount from about 1 to about 20 wt % of the fiber. In another exemplary embodiment, the anti-tack may be a combination of a bis-stearamide type anti-tack agent and one or more of another anti-tack agent, such as, but not limited to, $TiO_2$, talc, and corn starch, where the combined amount of anti-tack agents is about 1 to about 30 wt % of the fiber. In some exemplary embodiments the amount of anti-tack agent(s) is about 0.5 to about 30%, about 1 to about 20%, about 1 to about 5%, or about 2 to about 4% by weight of the fiber.

These anti-tack agents are added to the elastomeric polymer composition prior to spinning of the fiber such that the anti-tack agent is incorporated into the fiber. For instance, the anti-tack may be added upstream of the melt spinning process, such as during the formation of the elastomeric propylene based polymer, or it may be added during the melt-spinning process prior to fiber formation (e.g., during melt mixing).

Optional Additives

In embodiments of the fibers of the present disclosure, the fiber includes up to about 60 to about 9.5% by weight of elastomeric propylene based polymer composition, and the anti-tack agents are incorporated in the amount discussed above (e.g., about 0.5 to about 30% by weight of the fiber). In addition, the elastomeric fiber of the present disclosure may also include additional conventional additives for various purposes. Some such additives also may help to reduce tackiness. Suitable additives include, but are not limited to, organic stearates (e.g., calcium stearate or magnesium stearate), mineral oil, and mixtures thereof. While the elastomeric fiber of the present disclosure is substantially free of silicone-based finishing agents, in some embodiments, the elastomeric fiber may or may not include a non-silicone based spin finish, which includes, but is not limited to, a topically applied mineral oil finish or ester or fatty acid-based oil finishes or mixtures thereof. In embodiments, such non-silicone based finishes are applied in an amount of about 1% and about 7% by weight of the final fiber (i.e., weight once applied). In some embodiments the elastomeric fiber is substantially free of free of any finishing agent.

In an embodiment, the elastic fiber of the present disclosure may contain additional, conventional additives that are added for specific purposes, such as antioxidants, thermal stabilizers, UV stabilizers, pigments and delusterants (for example titanium dioxide), dyes and dye enhancers, additives to enhance resistance to chlorine degradation (for example zinc oxide; magnesium oxide and mixtures of huntite and hydromagnesite), and the like, so long as such additives do not produce antagonistic effects with the propylene based elastomer or anti-tack additive of this disclosure. Some of the conventional additives may exhibit small effects on over-end take-off tension (OETOT) measurements, one parameter used to judge tackiness of the elastic fiber, but none of them are added in amounts that would result in an appreciable effect on the OETOT measurements.

Preparing the Fibers and Articles

Embodiments of the present disclosure include a process for preparing any one of the elastomeric fibers as described herein. The process comprises providing an elastomeric propylene based polymer as described above. In embodiments, the elastomeric propylene based polymer may include a diene and/or a cross-linking agent, thus making the polymer composition cross-linkable. Next, the process includes adding/mixing an anti-tack agent described above (e.g., a bis-stearamide, $TiO_2$, corn-starch, talc, or mixtures thereof) to the elastomeric propylene based polymer composition. This mixing can occur during preparation of the elastomeric propylene based polymer or during melt-spinning. Next, the process includes preparing a fiber from the composition by a melt spinning process, where the resultant fiber can be unwound without the application of a silicone-based finish to the surface of the fiber prior to winding.

In an embodiment, during or after synthesizing the elastomeric polymer composition of the present disclosure, the anti-tack additive is incorporated into the composition. The composition having the anti-tack additive dispersed therein may be melt-spun to form the elastomeric fiber of the present disclosure. Melt-spinning refers to the process of melting a polymer composition and pushing the melted polymer solution through spinneret (die) orifices to form fibers (filaments), which are then cooled, solidified, and wound on a cylindrical core to form a yarn supply package. In other embodiment, the anti-tack additive is mixed with the polymer composition during the melt-spinning process at a point before the polymer composition is formed into a fiber, such as during the melt process. Thus, whether the anti-tack additive is incorporated into the elastomeric polymer composition upstream of the melt-spinning process or during the melt process, the additive is incorporated into the formed fiber as opposed to being applied to the surface of a formed fiber as in the case of a finishing agent.

In embodiments where the elastomeric polymer is cross-linkable by the inclusion of a diene and/or cross-linking agent, the method of producing the fiber of the present disclosure may further include cross-linking the fiber at some point after spinning the fiber. The fiber may be cross-linked after spinning but before being wound onto the package, or, the fiber may be cross-linked at some point down-stream of fiber formation, such as before being incorporated into an end-use article (e.g., fabric, laminate, apparel, disposable personal care article, and the like) or after the fiber has been incorporated into an end-use article. Cross-linking may be accomplished by various methods known to those of skill in the art, including, but not limited to heat, chemical catalysis, e-beaming, and the like. In an embodiment, cross-linking is achieved by exposing the fiber of the present disclosure to e-beam radiation. Other cross linking methods includes gamma radiation, heat, UV light, gamma irradiation, x-ray irradiation, UV (ultraviolet light), and the like, or combinations thereof.

Articles

Embodiments of the present disclosure include articles of manufacture comprising the elastic fiber of the present disclosure. These articles of manufacture include, but are not limited to, a fabric and a laminate structure.

In an embodiment, the present disclosure provides a fabric including the elastomeric fiber of the present disclosure, which includes elastomeric propylene based polymer as described above, an anti-tack agent described above, where the fiber is substantially free of a silicone-based finish on the surface of the fiber. The fabric of the present disclosure may be used to make a variety of end-use articles, such as, but not limited to, apparel, upholstery fabric, and the like.

In an embodiment, a laminate structure of the present disclosure includes the elastomeric fiber of the present disclosure, which includes elastomeric propylene based polymer as described above, an anti-tack agent described above, where the fiber is substantially free of a silicone-based finish on the surface of the fiber. In certain embodiments, the fiber is adhered to one or more layers of a substrate, such as a fabric, nonwoven, film, and combinations thereof. The laminate structure may be adhered by an adhesive, ultrasonic bonding, or combinations thereof. The laminate structure may be used to make a variety of articles, such as, but not limited to, disposable hygiene article such as diapers, training pants, adult incontinence articles, or feminine hygiene articles.

EXAMPLES

Having described the embodiments of the present disclosure, in general, the following Examples describe some additional embodiments of the present disclosure. While embodiments of present disclosure are described in connection with the following examples and the corresponding text and figures, there is no intent to limit embodiments of the present disclosure to this description. On the contrary, the intent is to cover all alternatives, modifications, and equivalents included within the spirit and scope of embodiments of the present disclosure.

Elastomeric fibers with and without an anti-tack additive were prepared according to the following methods. All fibers were made from an elastomeric propylene based polymer. Vistamaxx™ 1100 grade elastomeric propylene-based polymer (VM1100) (Examples 1-9) or Vistamaxx™ 2100 grade elastomeric propylene-based polymer (VM2100) (Examples 10-12) was used to spin the fibers, as indicated in Table 1, below. The fibers were melt spun and collected on a spool. Melt spinning was performed as described below.

A Fourné Pilot Melt Spinning system with an IWKA wind-up was used. This spinning apparatus is shown in FIG. 1. Polyolefin resin in the form of polymer chips was feed to an extruder. The resin was completely melted inside the extruder and then transported inside a heated and insulated transferline to a metering pump, which meters the polymer by an exact rate to a spinneret inside a spin pack, which is installed inside a spin block (aka "spin head"). The metering pump is insulated, and the pump block is heated electrically and also insulated to maintain a constant temperature.

In the following examples, a single extruder was used to supply molten polymer to two metering pumps, though more than one extruder could be used. Each metering pump has one inlet port and four outlet streams, hence a total of 8 polymer streams were metered simultaneously to 8 individual spinnerets. A total of 4 spin packs were installed inside the spin block, and each spin pack contains two individual spinnerets and screen filter assemblies. In practice, however, any combination of spinnerets per spin pack can be used satisfactorily. Each spinneret contains a single round capillary; however, a spinneret having multiple capillaries or a non-round x-section can also be used to make continuous yarns having multiple filaments or non-round x-section.

Upon being extruded from the spinneret capillary, the still-molten polymer was quenched by cooling air into solid fibers. In the following examples, two individual quench zones were used to enable complete quenching of the yarn (especially yarn having high dpf) and to allow some control for quench air flow profiling to optimize yarn uniformity. Each quench zone includes a blower, a duct with manually controlled dampers to allow control of gas flow rate, and a quench screen to direct and diffuse the air flow to quench the fibers efficiently and uniformly.

After the fibers were quenched and solidified, they were subsequently taken up by two driven rolls and wound up on a winder. Roll speeds were controlled such that yarn tension is optimal for winding the yarn onto a package and also for desired yarn property development. In this example, when finish is applied to the yarn (e.g., Examples 9 and 11) it was applied between the first and second roll using a roll applicator. However, other types of finish applicator can also be used, such as metered finish tips.

Exxon VM1100 resin, as used in examples 1-9 (Table 1), was also used to make 25, 40, 55, and 70 D single-filament elastic yarns with surprisingly high elongation and excellent yarn strength (data not shown). The results were both surprising and counter intuitive, in that VM1100 has very high intrinsic and melt viscosities, and is generally believed to be not suitable for spinning into filament yarn. It was discovered, however, that when this polymer was melted and maintained at an extremely high temperature range, it could be extruded into continuous filament yarns with surprisingly excellent spinning continuity and yarn properties. It was also surprising that fibers of suitable properties could be spun in a large range of dpf from 20 to 100 and possibly higher (whereas Spandex yarns typically limited to 10 dpf or lower to maintain desirable properties).

Unwinding was performed via both rolling takeoff and over end take of (OETO). Ease of unwinding was evaluated. Additives, such as the anti-tack additives described in the present disclosure, and/or finishing agents were added and/or applied to the fiber as described below. The amounts of the additives are given as weight percents based on total fiber weight.

For comparative Example 9, VM1100 was melt spun using no additives but utilizing a low viscosity silicone oil finish with magnesium stearate. The material formed a fiber, was able to be collected on a spool, and was able to be unwound from the spool without breaks both via a rolling takeoff and OETO.

In Examples 1 and 2 the elastomeric fiber of the present disclosure was prepared by use of VM1100 mixed with 3 wt. % of the anti-tack additive Ceridust 3910. The resin was able to be melt-spun, collected on a spool and subsequently unwound, without the application of any finishing agent. The fibers of examples 5-8 were prepared as in Examples 1 and 2 but with the addition of 6 wt % Ceridust 3910 (Examples 5-8) also allowed the resin to be melt spun, collected on a spool and subsequently unwound with even greater ease. In Examples 3 and 4, the anti-tack additive was 1 wt % $TiO_2$, and the resin was able to be melt spun, collected and unwound with out the application of a finishing agent.

For Example 11 a fiber was spun from VM2100 with the addition of 1 wt % Ceridust 3910 as the anti-tack additive, with the application of low viscosity silicone oil finish with magnesium stearate to the spun fiber. In comparative Example 10 this same polyolefin elastomer was melt spun and collected without additives or applied finish, and it was not able to be unwound by any means. For Example 12, the fiber was prepared as in Example 11 but without the addition of the finishing agent, and the fiber was also successfully, spun, collected and unwound. The results are presented in Table 1 below.

TABLE 1

| Ex. | Part | Doff | Plymr | MFR | Antitack | Finish | Spun Y/N | Unw. Y/N |
|---|---|---|---|---|---|---|---|---|
| 1 | VM1100 | 319 | VM1100 | 3 | 3% Ceridust 3910 | none | Y | Y |
| 2 | VM1100 | 321 | VM1100 | 3 | 3% Ceridust 3910 | none | Y | Y |
| 3 | VM1100 | 323 | VM1100 | 3 | 1% $TiO_2$ | none | Y | Y |
| 4 | VM1100 | 325 | VM1100 | 3 | 1% $TiO_2$ | none | Y | Y |

TABLE 1-continued

| Ex. | Part | Doff | Plymr | MFR | Antitack | Finish | Spun Y/N | Unw. Y/N |
|---|---|---|---|---|---|---|---|---|
| 5 | VM1100 | 326 | VM1100 | 3 | 6% Ceridust 3910 | none | Y | Y |
| 6 | VM1100 | 327 | VM1100 | 3 | 6% Ceridust 3910 | none | Y | Y |
| 7 | VM1100 | 328 | VM1100 | 3 | 6% Ceridust 3910 | none | Y | Y |
| 8 | VM1100 | 329 | VM1100 | 3 | 6% Ceridust 3910 | none | Y | Y |
| 9 | 110002 | 83 | VM1100 | 3 | No additives | LY-19 | Y | Y |
| 10 | NF2100 | | VM2100 | 21 | No finish | none | Y | N |
| 11 | 210009 | 1 | VM2100 | 21 | 1% Ceridust 3910 | LY-19 | Y | Y |
| 12 | 210011 | 1 | VM2100 | 21 | 1% Ceridust 3910 | none | Y | Y |

These data demonstrate that fibers spun from a mixture of an elastomeric propylene based polymer and an anti-tack agent (such as an ethylene bis-stearamide or $TiO_2$), are able to be spun, wound and subsequently unwound without the need for a finishing-agent.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also the individual concentrations (e.g., 1%, 2%, 3%, and 4%) and the sub-ranges (e.g., 0.5%, 1.1%, 2.2%, 3.3%, and 4.4%) within the indicated range. The term "about" can include ±1%, ±2%, ±3%, ±4%, ±5%, ±8%, or ±10%, of the numerical value(s) being modified. In addition, the phrase "about 'x' to 'y'" includes "about 'x' to about 'y'".

Many variations and modifications may be made to the above-described embodiments. All such modifications and variations are intended to be included herein within the scope of this disclosure and protected by the following claims.

The invention claimed is:

1. A yarn comprising a fiber consisting of:
   an elastomeric propylene based polymer;
   an anti-tack agent, wherein the anti-tack agent is a bis-stearamide in combination with another anti-tack agent selected from the group consisting of $TiO_2$, corn starch, talc, barium sulfate, lamellar clay, and calcium carbonate;
   a diene selected from the group consisting of 5-ethylidene-2-norbornene (ENB); 1,4-hexadiene; 5-methylene-2-norbornene (MNB); 1,6-octadiene; 5-methyl-1,4-hexadiene; 3,7-dimethyl-1,6-octadiene; 1,3-cyclopentadiene; 1,4-cyclohexadiene; vinyl norbornene (VNB); dicyclopentadiene (DCPD), and a combination thereof;
   a non-silicone finishing agent on a surface of the fiber, said fiber having less than 0.01 weight % of a silicone-based finishing agent on the surface of the fiber;
   optionally an additive selected from an antioxidant, thermal stabilizer, UV stabilizer, pigment, delustrant, dye, dye enhancer and/or additive to enhance resistance to chlorine degradation; and
   optionally a crosslinking agent selected from the group consisting of: a multifunctional acrylate, a multifunctional methacrylate, a functionalized polybutadiene resin, a functionalized cyanurate, and allyl isocyanurate;
   wherein the anti-tack agent is present in an amount of about 0.5 to about 30% by weight of the fiber;
   wherein said anti-tack agent is blended with said elastomeric propylene-based polymer prior to spinning; and
   wherein said yarn is spun, wound and unwound on a yarn package without sticking together.

2. The yarn of claim 1, wherein the bis-stearamide is selected from the group consisting of bi-stearyl-ethylenediamide; N,N'-ethylene bisstearamide; N,N'-ethylene bis(octadecanamide); 1,2-bis(octadecanamido) ethane; and a combination thereof.

3. The yarn of claim 1, wherein the non-silicone based finishing agent comprises an ester based oil finish or a fatty acid based oil finish or a combination thereof.

4. The yarn of claim 1, wherein the fiber is at least partially crosslinked.

5. The yarn of claim 1, wherein the anti-tack agent is an ethylene bis-stearamide.

6. The yarn of claim 5, wherein the ethylene bis-stearamide is present in an amount of about 1 to about 10% by weight of the fiber.

7. An article comprising the yarn of claim 1.

* * * * *